US008955720B2

(12) United States Patent
Herold et al.

(10) Patent No.: US 8,955,720 B2
(45) Date of Patent: Feb. 17, 2015

(54) CONTAINER FOR FLOWABLE SUBSTANCES AND DISPENSING APPARATUS

(75) Inventors: Wolf Herold, Diessen (DE); Stephan Neuhaus, Augsburg (DE)

(73) Assignee: Delo Industrieklebstoffe GmbH & Co. KGAA, Windach (DE)

( * ) Notice: Subject to any disclaimer, the term of this patent is extended or adjusted under 35 U.S.C. 154(b) by 295 days.

(21) Appl. No.: 12/864,802

(22) PCT Filed: Mar. 13, 2009

(86) PCT No.: PCT/EP2009/053010
§ 371 (c)(1),
(2), (4) Date: Jul. 27, 2010

(87) PCT Pub. No.: WO2009/115467
PCT Pub. Date: Sep. 24, 2009

(65) Prior Publication Data
US 2010/0308075 A1    Dec. 9, 2010

(30) Foreign Application Priority Data
Mar. 18, 2008  (DE) .......................... 10 2008 014 773

(51) Int. Cl.
*G01F 11/00* (2006.01)
*B65D 47/26* (2006.01)
(Continued)

(52) U.S. Cl.
CPC .......... *B65D 47/265* (2013.01); *B65D 83/0094* (2013.01); *G01F 23/261* (2013.01); *G01F 23/265* (2013.01); *A61M 2039/229* (2013.01)
USPC ......... 222/386.5; 222/105; 222/389; 220/723

(58) Field of Classification Search
USPC ............... 222/1, 386.5, 145.1, 389, 253, 444, 222/64–66, 52, 157, 47, 51, 228, 206, 212, 222/213, 215, 339; 220/4.25, 720–723; 138/30; 141/128; 73/304, 1.31, 1.73, 73/304 R, 304 C; 324/698; 53/452
See application file for complete search history.

(56) References Cited

U.S. PATENT DOCUMENTS 3,158,296 A * 11/1964 Cornelius .................. 222/386.5
3,656,662 A *  4/1972 Peterson .................... 222/386.5
(Continued)

FOREIGN PATENT DOCUMENTS

CN    605 328        9/1978
DE    9103038 U1     7/1992
(Continued)

OTHER PUBLICATIONS

Notification of Transmittal of Translation of the International Preliminary Report on Patentability for PCT/EP2009/053010, Mar. 13, 2009.
(Continued)

*Primary Examiner* — Frederick C Nicolas
*Assistant Examiner* — Bob Zadeh
(74) *Attorney, Agent, or Firm* — Barnes & Thornburg LLP

(57) ABSTRACT

A container for flowable substances includes a rigid, concave lower part having an outlet and an upper part including of a convex flexible film that is mirror-inverted with respect to the inner contour of the lower part. The upper and lower parts may be in the shape of hemispheres. The upper part is surrounded by a housing body which is tightly connected with the lower part and may be connected to a pressure source for emptying the container. In the emptied condition of the container, the film lies flush at the inner contour of the lower part of the container. For emptying, air pressure is applied to the upper part of the container. The outlet is provided with a closure in the shape of a disc which is rotatable about an axis offset from the opening of the outlet and has a passage for inserting a dispensing nipple.

9 Claims, 6 Drawing Sheets

(51) Int. Cl.
 *B65D 83/00* (2006.01)
 *G01F 23/26* (2006.01)
 *A61M 39/22* (2006.01)

(56) References Cited

U.S. PATENT DOCUMENTS

| | | | |
|---|---|---|---|
| 3,849,771 A * | 11/1974 | Applin | 340/624 |
| 3,862,708 A * | 1/1975 | Waxlax | 222/444 |
| 3,940,031 A * | 2/1976 | Fishman | 222/386.5 |
| 3,945,539 A * | 3/1976 | Sossong | 222/386.5 |
| 4,252,151 A * | 2/1981 | Haug et al. | 138/30 |
| 4,282,986 A | 8/1981 | af Ekenstam et al. | |
| 4,325,369 A | 4/1982 | Nilson | |
| 4,335,751 A * | 6/1982 | Sugimura et al. | 138/30 |
| 5,017,909 A * | 5/1991 | Goekler | 340/620 |
| 5,135,485 A * | 8/1992 | Cohen et al. | 604/67 |
| 5,203,470 A * | 4/1993 | Brown | 229/117.3 |
| 5,230,438 A * | 7/1993 | Kind et al. | 220/240 |
| 6,129,236 A * | 10/2000 | Osokin et al. | 220/723 |
| 7,059,487 B2 | 6/2006 | Ohlsson | |
| 7,127,943 B1 * | 10/2006 | Griffiths et al. | 73/304 C |
| 7,377,162 B2 * | 5/2008 | Lazaris | 73/313 |
| 7,509,856 B1 * | 3/2009 | Winkens et al. | 73/304 C |
| 7,726,511 B2 * | 6/2010 | Beall | 220/723 |
| 7,802,471 B2 * | 9/2010 | Sieh et al. | 73/304 C |
| 2004/0094572 A1 * | 5/2004 | Rubinstein | 222/95 |
| 2008/0105708 A1 * | 5/2008 | Ebikawa et al. | 222/145.1 |
| 2009/0188109 A1 * | 7/2009 | Bampton et al. | 29/890.01 |

FOREIGN PATENT DOCUMENTS

| | | |
|---|---|---|
| DE | 2 268 231 | 1/1994 |
| DE | 4335970 A1 | 4/1995 |
| DE | 19513223 A1 | 10/1996 |
| DE | 19810217 A1 | 9/1999 |
| DE | 10311080 A1 | 9/2004 |
| EP | 0541972 A1 | 5/1993 |
| EP | 0787655 A1 | 8/1997 |
| EP | 1331174 A1 | 7/2003 |
| GB | 1576126 | 10/1980 |
| GB | 2 268 231 | 1/1994 |
| JP | 07171461 A | 7/1995 |
| NL | 7602203 | 9/1976 |

OTHER PUBLICATIONS

International Search Report mailed Jul. 2, 2009 for International Application No. PCT/EP2009/053010.

* cited by examiner

CONTAINER FOR FLOWABLE SUBSTANCES AND DISPENSING APPARATUS

CROSS-REFERENCE TO RELATED APPLICATIONS

This applications claims the benefit of priority to International Patent Application No. PCT/EP2009/053010 filed 13 Mar. 2009, which further claims the benefit of priority to German Patent Application No. 102008014773.7 filed 18 Mar. 2009, the entire contents of which are incorporated herein by reference.

DESCRIPTION OF THE PRIOR ART

In metering flowable substances (e.g., adhesives, sealing and moulding materials) in electronics applications, in dentistry or in the general joining technology, it is of crucial significance that the substrate is applied absolutely free of bubbles. Specifically in an automatic production process, where minute quantities of a substance are applied on a substrate, air bubbles existing in the adhesive result in defective parts, i.e., rejects.

In addition to the necessity of having all parts checked and faulty items sorted out, the occurrence of bubbles usually requires the entire line to be stopped and cleaned in a time-consuming way. The smaller the metered quantities the more rejects are produced when bubbles occur.

Expensive adhesives and sealants and dental moulding materials are often offered to customers in commercially available rigid disposable cartridges as primary containers. Such cartridges are emptied by means of a piston which is advanced either mechanically or by compressed air. Experience teaches that cartridges which were filled and sealed in a bubble-free manner arrive at the customer full of bubbles.

This is explained as follows: Many one-component adhesives must be cooled or deep-frozen during their entire storage time to prevent premature curing. At temperatures below room temperature, the difference in thermal expansion coefficients causes the liquid to shrink more than the rigid plastics material of the primary container. At low temperatures, the liquid substance will turn into a solid block which partly separates from the cartridge wall. This process creates a vacuum within the cartridge chamber, which will suck air into the cartridge through the friction-fitted, immobile closure piston and, possibly, also through the front closure. When the content of the cartridge is re-melted, air bubbles will be found throughout the liquid substance. When the cartridge is frozen and re-melted several times, the gradually retreating closure piston will each time draw more and more air into the chamber.

The same action is observed with substances which do not require deep-freezing. If an adhesive is filled in a vessel at room temperature it will expand during storage at a higher temperature (e.g., in summer). It will then push back the friction-fitted but movable closure plug. When subsequently cooled down to room temperature, the adhesive will shrink while the closure plug will be retained by friction in its withdrawn position. This creates a vacuum that will draw air into the chamber past the piston. If this cartridge is shipped by air cargo, the temperature change occurring at every starting and landing will cause the closure plug to move backward by a noticeable distance.

As a result, it must be assumed that cartridges originally filled in an absolutely bubble-free manner, after storage and transport are not free from bubbles when available to the user, and that serious problem are encountered when these cartridges are used in production.

An originally bubble-free viscous liquid can be full of bubbles if an open package (such as an open bottle or a cartridge without a piston) is exposed over an extended period of time to pressurized air for metering. Over the time, an increasing portion of the pressurized gas will dissolve in the substance. When this substance, upon leaving the metering valve, is exposed to the normal atmospheric pressure, the dissolved gas will expand and many small air bubbles will be found in the previously bubble-free substance.

The same phenomenon is observed with a filled cartridge which has a piston and is emptied by means of pressurized air. If there is a leak between the advancing piston and the cartridge wall, pressurized air will pass the piston to reach the liquid and over the time dissolve in the material.

There may be ways to achieve a permanently save freedom of bubbles in a flowable substance contained in a metering container even under changing temperatures if the rigid wall of a cartridge is replaced by a flexible film. In accordance with, e.g., DE 103 11 080 A1, the flowable substance is still contained in a conventional rigid cartridge; however, the closure piston is made of a solid outer ring with the piston head consisting of a flexible film. Changes in the volume of the substance due to temperature are taken up by the flexible film without any movement of the piston. It is a disadvantage of this solution that, when emptied by means of pressurized air, air will enter the filling substance, passing between the piston ring and the cartridge wall. On the other hand, when the filling substance is pressed out mechanically, high pressure may push the substance rearward past the piston, which causes contamination and loss of substance.

Commercially available packages for flowable substances, such as dental substances, adhesives and sealing materials, are thin composite films which are closed by metallic clips at the front and rear ends; compare EP 0 541 972 A1, DE 91 03 038 U1, EP 0 787 655 A1, DE 43 35 970 A1. The filling is done in a bubble-free manner using a conventional "sausage stuffing" equipment.

To ensure precise and clean emptying, these cylindrical tubular bags are provided at one end with a dispensing port which is usually slid onto the bag and glued thereto. For emptying, the film is mechanically cut within the area of the dispensing port.

This type of film container has two essential disadvantages.

It has been found that the metallic end closures are never tight with respect to thin flowing materials or components. This is due to the fact that the composite film, which has been formed into the hose, must be reduced from a large diameter to a very small diameter. The folds, which are thus necessarily created, permit small amounts of liquid to escape even when very strong closure clips are used. Over an extended storage time, low-viscosity components of the filling substance escape by capillary action and contaminate the whole bag. To protect the packaging and the user's hand during unpacking, film containers of this type are preferably shipped in plastic bags. As another disadvantage, the composition of the originally filled material changes due to the escape of the low-viscosity component.

The escape of a liquid component at the leaky locations of this film bag is increased when the container is emptied by a dispensing device. In this case, high dispensing forces are exerted on the film bag, and the liquid dispensed under such pressure will contaminate the dispensing device.

The second essential disadvantage of this film container with respect to bubble-free metering resides in the fact that air is trapped in the folds between the film folded at the container end and the dispensing port glued thereto, which air cannot be removed. When a film bag is automatically perforated by means of a spike (EP 0 787 655 A1), a large volume of air further exists between the film bag and the end of the dispensing port. When the film container is emptied, this air will escape, driven by the dispensing forces, at unpredictable times in the form of air bubbles and produce waste.

Further, similar film containers are shown in JP 07 171 461 A and EP 1 331 174 A1.

The commercially available film containers have, as a common feature, a cylindrical film tube which is usually folded and welded into a hose. Dispensing is done by either pressurized air or a mechanically advanced piston. To prevent the thin film of the container or the welded seam from tearing under high dispensing pressures, the film bag is placed in a stable cylindrical sleeve. The inner diameter of the sleeve and the outer diameter of the film bag are to be matched very precisely. If the film hose is too large, it cannot be moved into the sleeve, whereas if it is too small, the film will be ruptured when emptied by pressure.

When the cartridge is emptied, the internal pressure generated will strongly press the film hose of the container against the wall of the sleeve. When emptying the cartridge, the film is axially moved along the sleeve wall whereby the film is folded in an uncontrolled manner. This means that high frictional forces are generated during emptying, which counteract the emptying force.

These frictional forces depend, on the one hand, on the viscosity of the filling material, the emptying force, the amount of overlap of the welded film and the difference between the outer diameter of the film bag and the inner diameter of the cartridge. They are further strongly dependent on the emptying process proper. For instance, they are small when the film bag starts to collapse, while they rise during the emptying process and increase extremely at the end of the emptying process.

If the cartridge is emptied by means of a constant air pressure, the metered amounts dispensed over a defined unit of time become very different due to the frictional effects mentioned above. For this reason, such a device is principally not useful for most metering jobs. Even with a mechanical advancement, strong variations of the amounts being dispensed must be expected.

There are further disadvantages in dispensing residual amounts. Due to the irregular formation of folds in the film during the emptying process, closed pockets will form and take up filling material which cannot be pressed out.

U.S. Pat. No. 4,282,986 dicloses a container for flowable substances, which comprises a rigid concave lower part provided with an outlet and an upper part consisting of a flexible film having a convex shape essentially mirror-inverted with respect to the inner contour of the lower part. This is specifically a container for drugs which permits simple handling also by older patients. It is not concerned with the problem of avoiding bubbles as explained above.

SUMMARY OF THE INVENTION

It is an object of the invention to provide a metering container for flowable substances, a device for emptying such a container and methods of filling and emptying the container, wherein the substance is assured to be free of bubbles during storage and shipping even under greatly changing temperatures and pressures and during emptying and changing the container.

It is also an object of the invention that uniformly metered amounts may be dispensed when a uniform dispensing pressure is applied over a predetermined unit of time. This uniformity of the metered amount being dispensed should be maintained throughout the metering process from the full container to the almost empty container.

To meet these objects a container for flowable substances comprises a rigid concave lower container portion provided with an outlet and an upper container portion formed by a flexible film having a convex shape essentially mirror-inverted with respect to the inner contour of the lower container portion, the outlet including a closure having a disc rotatable about an axis offset from an opening of the outlet, and a passage for receiving a dispensing nipple.

A device for emptying such a container comprises a vessel for receiving the container, a dispensing nipple adapted to be inserted in the passage of the closure, and means for creating pressure between the dispensing nipple and the container.

DETAILED DESCRIPTION

Figure 1:
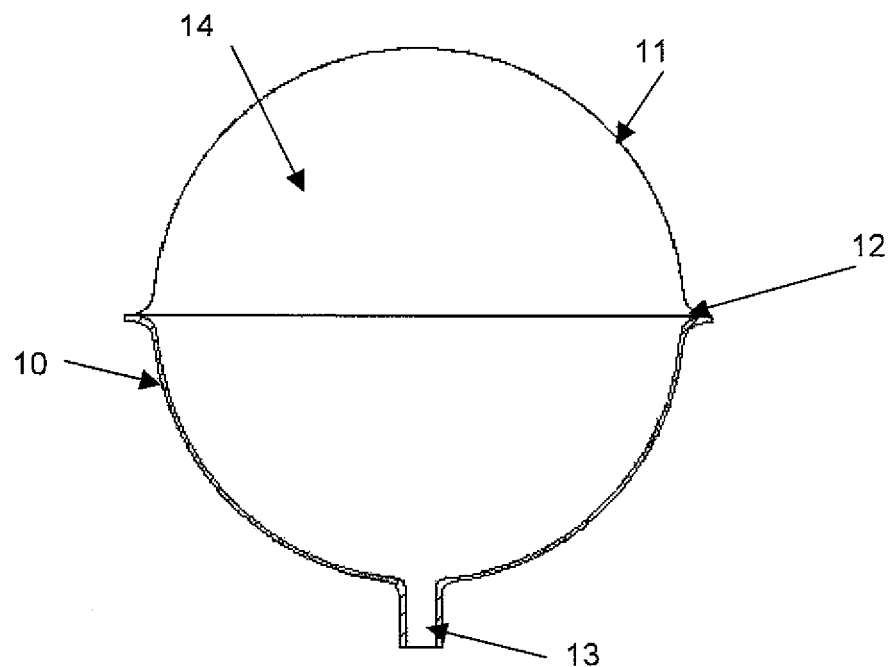
FIG. 1 is a longitudinal section through the main portion of a filled metering container for explaining the principle underlying the invention.

FIG. 1 shows the body of a metering container 14 without a pressure tank and without a closure. The lower part 10 of the container 14 consists of a rigid injection-moulded part of synthetic resin and may have a rotationally symmetrical (e.g., spherical) inner contour. The lower end may be provided with an outlet 13, which is only schematically shown in this figure, and the upper end may have a peripheral flange 12.

The upper part of the container 14 consists of a thin film 11 which may have a thickness of, e.g., between 50 µm and 500 µm, and may be shaped substantially mirror-inverted with respect to the inner contour of the lower part 10. The film 11 may be made of a material that is impermeable to the filling substance, e.g., a plastic film of PE or PET or a plastic composite film laminated with aluminium. The shape of the film 11 can be obtained by deep-drawing.

There may be substances which during storage require a certain amount of oxygen or another gas to prevent them from curing prematurely. Since such dissolved gas is consumed during storage, oxygen must be continuously supplied from the ambient air. If the film 11 is oxygen permeable, the supply of oxygen may take place continuously, uniformly and, specifically, across a large area.

The upper and lower parts may be hermetically sealed to one another by gluing or welding in the area of their largest diameter at the flange 12. If this device is filled through its inlet or outlet in a bubble-free manner and closed in an airtight fashion, the result is a metering container that is hermetically sealed against the ambience. Once filled and sealed, no air or foreign material can enter this container 14 during storage or shipment and no filling material can escape from the container 14. Volumetric changes of the filling substance caused by even extreme changes in temperature may be completely compensated by the flexibility of the thin film 11 so that no over pressure or vacuum will be generated within the container 14 itself.

Figure 2:
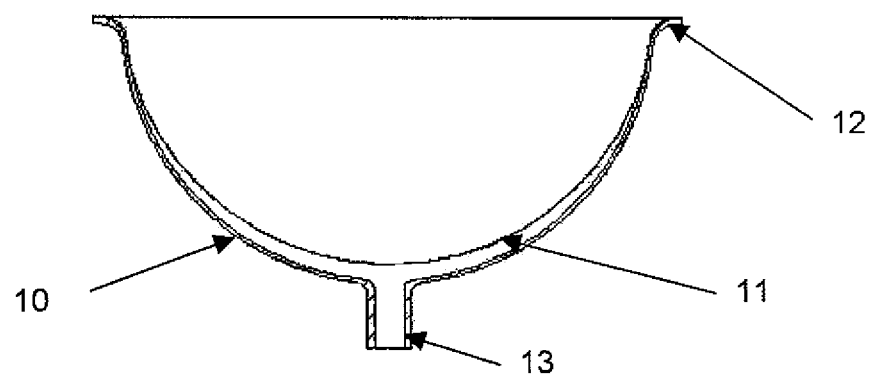
FIG. 2 is a section similar to FIG. 1 through the container prior to being filled.

FIG. 2 shows the container 14 prior to be filled with a liquid. The flexible film 11 is folded inward to lie flush at the inner contour of the lower part 10. Any residual amount of air at the outlet 13 is sucked by applying a vacuum. Subsequently, the liquid is pressed into the container 14 under vacuum.

Figure 3:
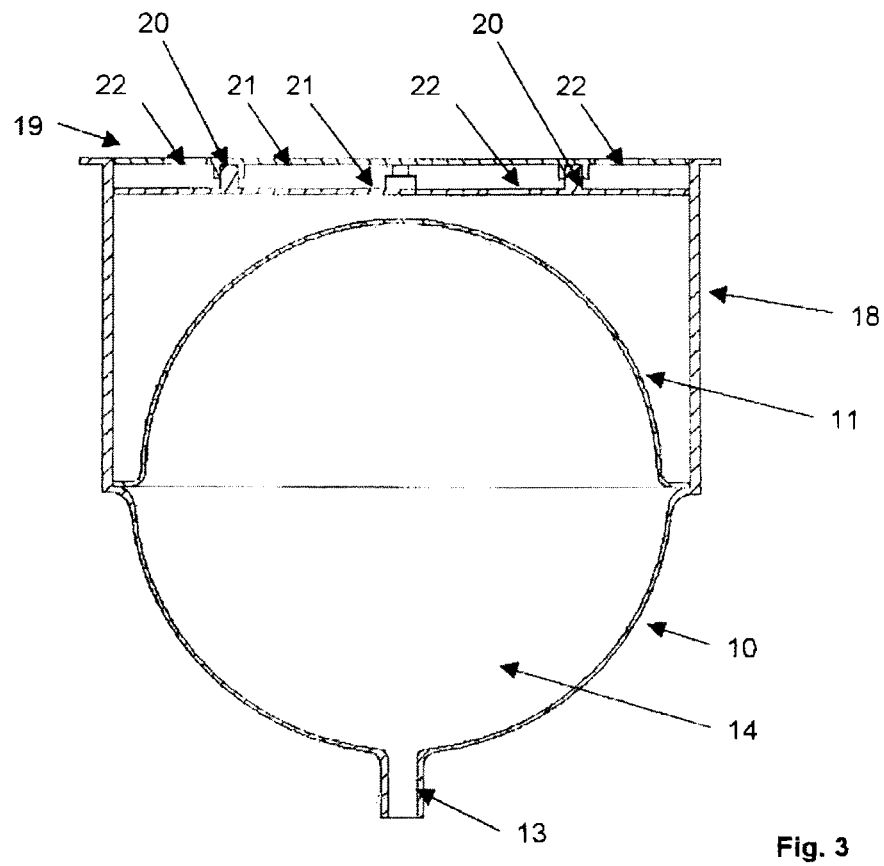
FIG. 3 is a section similar to FIG. 1 through the container including a pressure vessel.

FIG. 3 shows the container 14 with a cylindrical body 18 integrally formed with the flange 12 or tightly connected thereto, the upper end of the body 18 being closed by a double-walled cover 19. The body 18 and the cover 19 serve to protect the flexible film 11 against mechanical damages and incident light. The cover 19 is made of two disc-shaped walls 21 interconnected by a number of spacers 20 and having none-aligned pressure equalising holes 22.

To fill the container 14 in a bubble-free manner, the film 11 is pressed or sucked to the inner contour of the rigid lower part 10. The residual volume is exposed to vacuum through the outlet 13, and the container 14 is subsequently filled from below.

For emptying, the container 14 is connected to a pressure chamber or inserted into the same (as explained below with reference to FIG. 10), the pressure chamber sealingly surrounding at least the upper most part of the body 18. The pressurized air flowing through the holes 22 is uniformly applied to the film 11 and presses the liquid uniformly through the outlet 13 from the container 14. When the body 18 and the lower part 10 of the container may be thin-walled to save weight and cost, it is useful to form the pressure chamber in such a way that, during emptying, it surrounds the entire container 14 and the body 18 with the exception of the outlet 13.

Metered emptying of the container 14 is achieved by a uniform application of pressure to the film 11 (e.g., using pressurized air). The tight peripheral sealing at the flange 12 prevents air from entering the container 14. The film 11 itself will be deformed very uniformly throughout the emptying process without building up any resistance because there is no wall friction and because the film is not folded by an advance movement.

If pressure is applied to the film 11 via a hydraulic liquid, the container 14 is also suitable for volumetric metering.

When the emptying process terminates, the film 11 will lie flush at the inner contour of the lower part 10 of the container without folds. Since the film 11 is deformed without any forces throughout the emptying process, the metered amounts dispensed over a fixed unit of time under constant air pressure will be constant.

Figure 4:
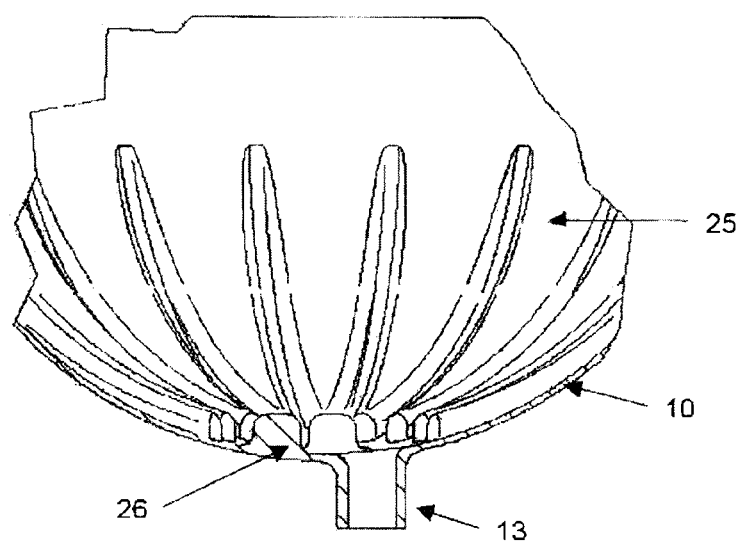
FIG. 4 is a partial section through the lower part of the container in a non-filled condition.

FIG. 4 shows the lower part 10 of the container 14 with grooves 25 radially extending toward the outlet 13 of the container 14. The grooves ensure that the amount of liquid dispensed over time remains constant until the container is completely empty. Protruding webs 26 may be provided near the outlet 13 to prevent the film 11 from impeding or inhibiting the complete emptying by blocking the opening of the outlet 13 near the end of the emptying process. The webs 26 hold the film 11 at a distance from the opening of the outlet 13 to make sure that the liquid can freely flow out until the container 14 is completely empty.

In an adhesive processing production line, information about the remaining quantity available is required particularly near the end of the container emptying process. Only this makes it possible to change containers in proper time and avoid incorrect metering. With conventional cartridges, this can be done by, e.g., detecting the position of a closure piston. This is not readily available with the present container 14 because its rear end is closed by the flexible film 11 rather than by a rigid piston. This film is irregularly deformed during emptying and may be therefore not readily available as a filling level indicator. However, toward the end of the emptying process, the film 11 will lie flush at the inner contour of the lower part 10.

Figure 5:
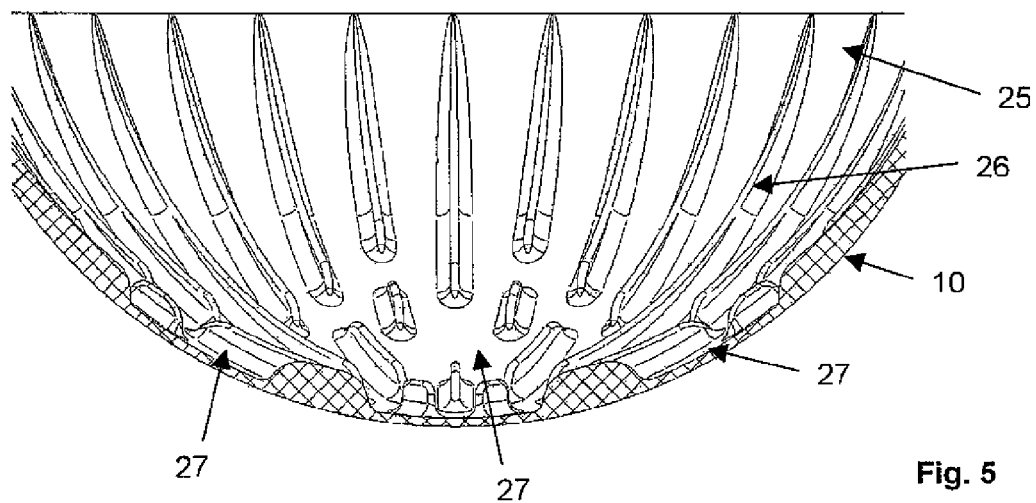
FIG. 5 is a partial section similar to FIG. 4 through the lower part of the container with interrupted grooves.

In the embodiment shown in FIG. 5, some of the webs 26 may be interrupted near the outlet 13 (not shown in this figure). Inductive or capacitive sensors 41 may be provided in these areas 27 at the outer side of the lower part 10, the sensor signals being supplied to an evaluation circuit (not shown).

Figure 6:
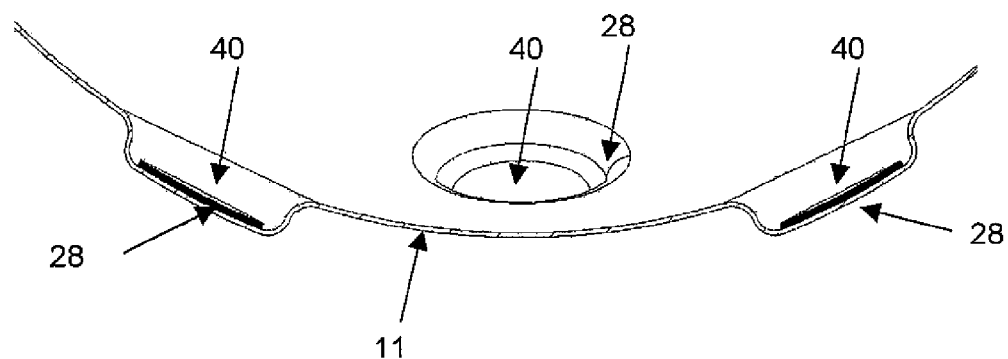
FIG. 6 is a section through the film, which is deep-drawn at a plurality of locations near the outlet.

As shown in FIG. 6, the film 11 may be provided with recesses 28 in the areas 27 of the lower part 10 of the container with metallic sheets 40, which may be circular, being placed in the recesses.

Figure 7:
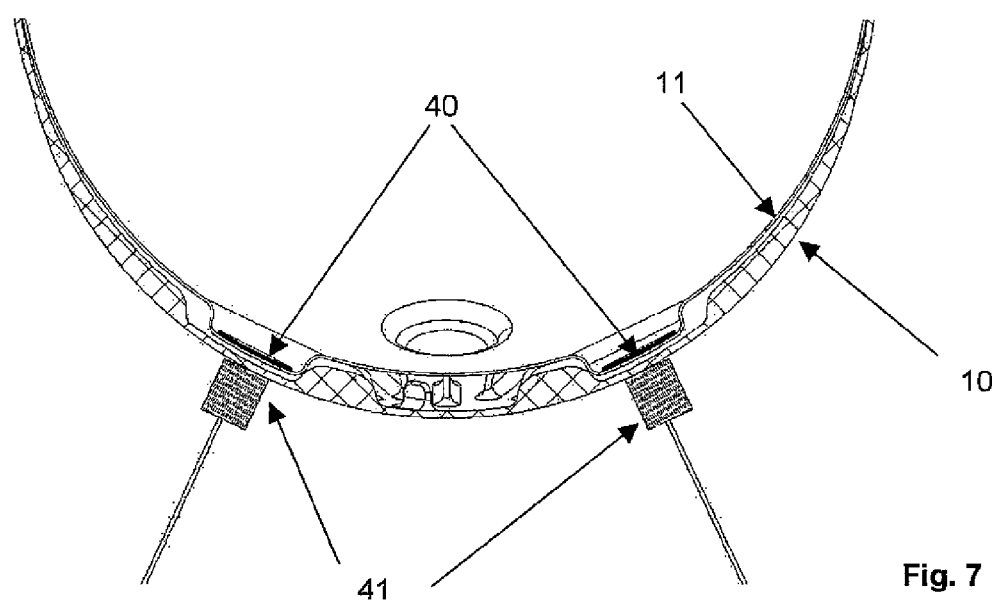
FIG. 7 shows the lower part of the container with filling level detectors.

FIG. 7 shows the lower part 10 in the emptied state in which the film 11 contacts the inner wall of the lower part 10. In this condition, the metallic sheets 40 may be detected by the sensors 41.

In this way, contact of the film 11 may be detected in the nearest environment of the container outlet 13 thereby providing an indication of the residual amount of adhesive. Since the film 11 will not uniformly contact the container wall at all locations, the position of the film may be detected at a plurality (e.g., four) peripheral locations. The evaluation circuit can operate in such a way that it provides a warning for the change of containers when the film 11 contacts one of these locations. If it contacts, for instance, three locations, the system may switch-off the entire line to avoid metering errors.

If it is intended to maintain the substance free of bubbles throughout the metering process until the substance may be dispensed from downstream metering valve, it may be necessary to ensure that no air enters the container 14 when the latter may be coupled to a supply hose of a metering system.

When commercially available cartridge closures may be used, the film 11 presents an additional problem when the above described container 14 may be opened. For instance, with low-viscosity products, when the closure cap is removed, the filling substance will flow out because it is not retained by the flexible film 11 as it would be by a cartridge piston. On the other hand, if the outlet is held upward, the container 14 will suck in air because of the weight of the filling substance and the flexible film 11.

Figure 8:
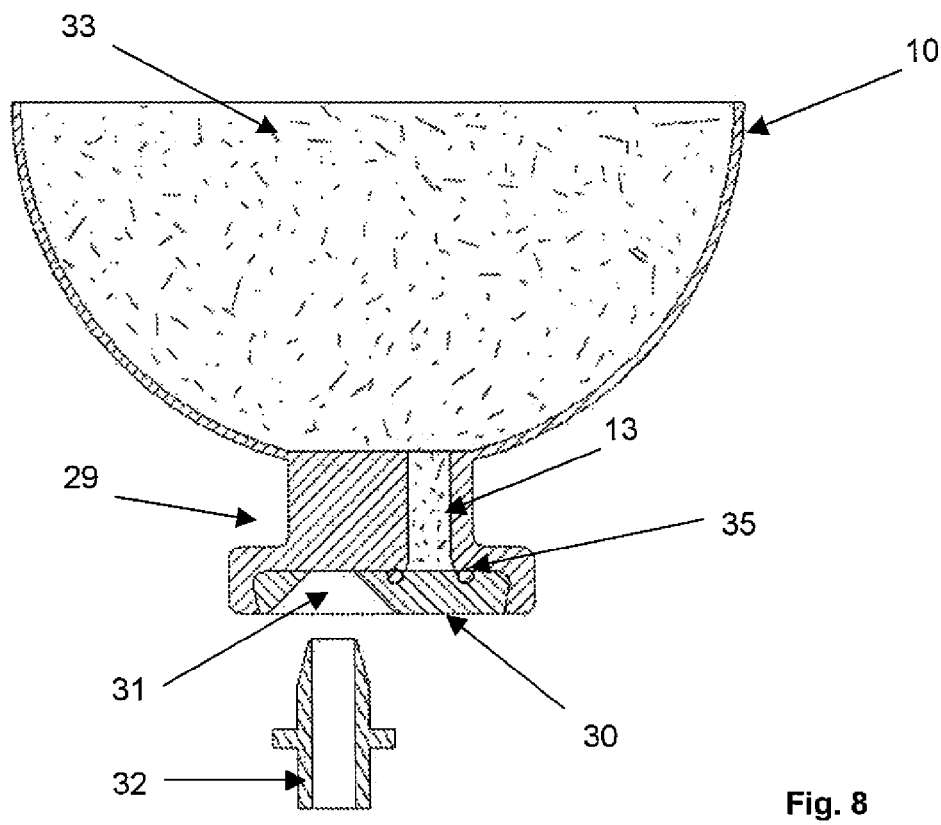
FIG. 8 is a section through the lower part of the container with a closure in the closed position.

To solve this problem, a disc 30 may be provided at the end at the outlet 13 at the lower part 10 of the container 14, as shown in FIG. 8, the plane surface of the disc hermetically closing the outlet 13. The liquid 33 of the container 14 contacts this plane without bubbles. A sealing lip 35 (e.g., an O-ring) provides maximum tightness during storage and shipping.

The rotationally symmetric disc 30 may be mounted for rotation about an axis which may be offset with respect to the outlet 13. The disc 30 has a passage 31 for receiving a nipple 32 of a supply hose. The passage 31 has a conical or calotte-shaped inward taper (upward in FIGS. 8 and 9) which may be shaped so that the difference between the diameter of the passage 31 and that of the nipple 32 decreases from an initially positive value to at least zero or less. This specific shape of the passage 31 prevents the formation of an air cushion when the nipple 32 may be inserted. The supply hose leads to the actual downstream metering valve (not shown).

Figure 9:
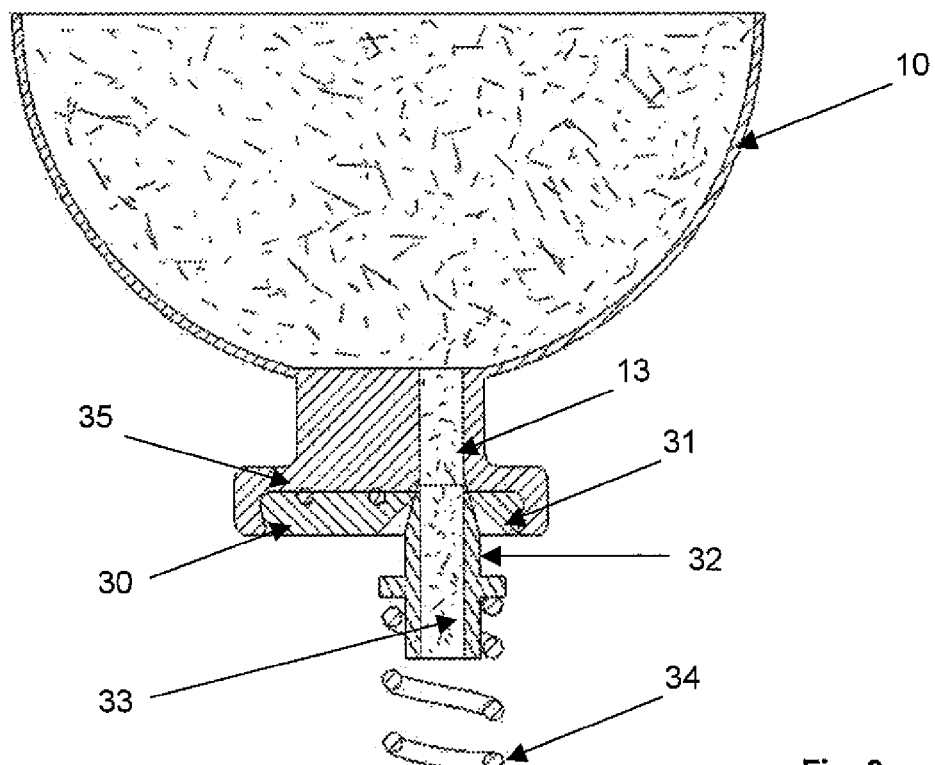
FIG. 9 is a section through the lower part of the container showing the closure in the open position.

By rotating the disc 30 about its axis, the nipple 32 may be moved directly under the outlet 13 of the container 14 and may be pressed by a spring 34 a small distance into the passage 31 (FIG. 9). If the supply hose was completely filled with liquid, it may be certain that no air enters the supply line while it is being connected. Because the outlet 13 is thus not open toward the environment at any time, substance can never flow out and air can never be sucked in. Thus, the behaviour of the film described above has no effect. Connecting and changing a metering container 14 take place in a bubble-free manner.

In practice, it may be possible that metering containers may be emptied only in part during a production day. Such partially filled containers must be stored in a refrigerated or frozen condition overnight, over a weekend or until the next production order may be processed. The arrangement shown in FIGS. 8 and 9 prevents undesired air bubbles from entering into the supply line and ensures a reliable and bubble-free production process even when partially filled metering containers 14 may be removed and re-connected.

Figure 10:
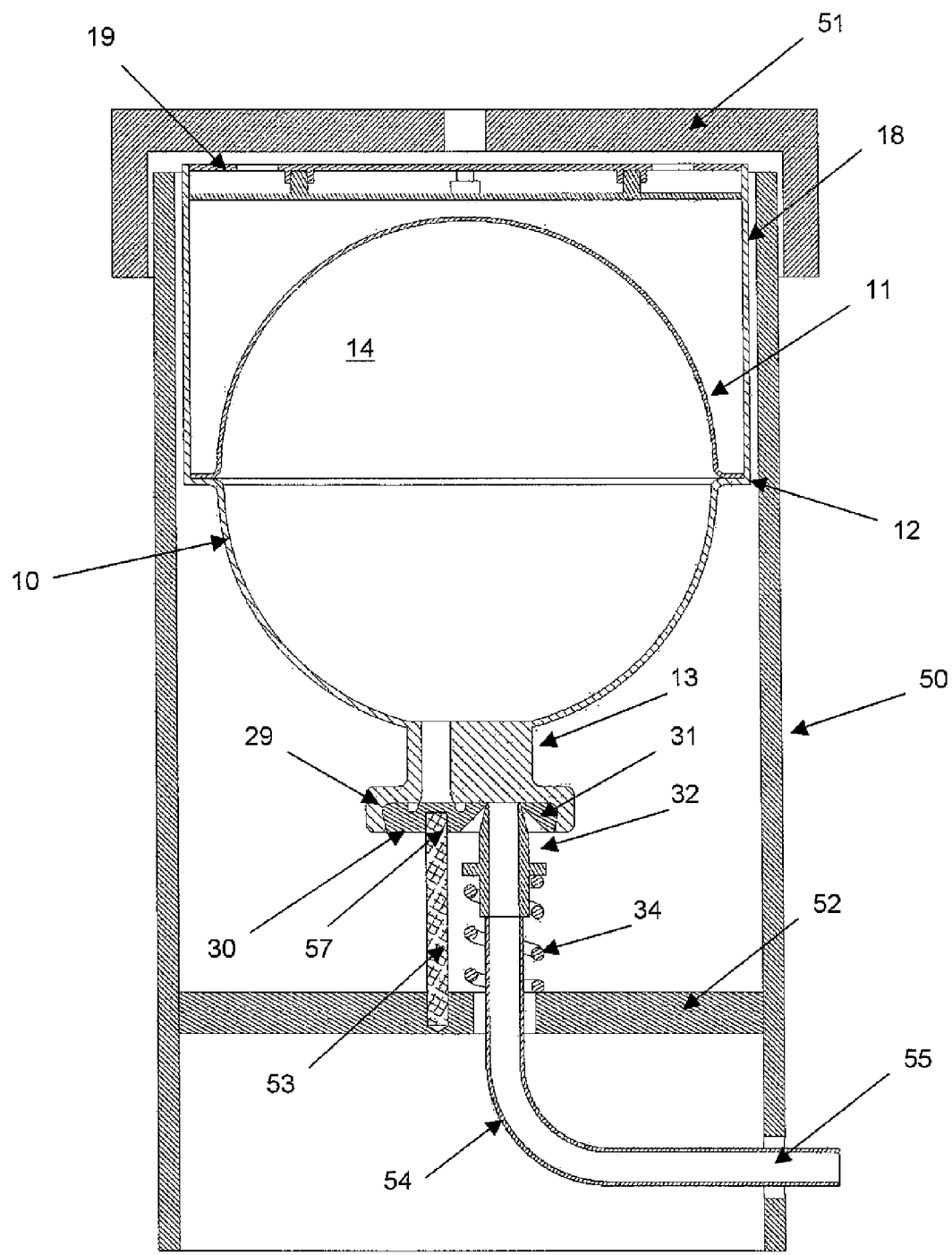
FIG. 10 is a schematic representation of an emptying device.

The emptying device shown schematically in FIG. 10 comprises a pressure vessel 50 with a bayonet-type lid 51 as known from EP 0 532 945 A1. The nipple 32 may be supported by an intermediate wall 52 through a compression spring 34, the wall 52 also carrying an upward projecting locking pin 53. A supply hose 54 coupled to the nipple 32 leads to an outer connecting piece 55.

The pressure vessel has such an inner diameter that it surrounds the container 14 placed therein with little clearance. When the lid 51 is closed, the container 14 which may be provided with the body 18 shown in FIG. 3 may be pressed downward onto the nipple 32 which may be biased by the spring 34 so that the nipple may be centred within the conical or calotte-shaped passage 31. Simultaneously, the locking pin 53 engages a stud hole 57 provided in the locking disc 30 of the container 14. For subsequent locking, the lid 51 may be rotated with respect to the pressure vessel 50 wherein the lid entrains the container 14 while the disc 30 is fixed by the locking pin 53. In this manner, the container 14 may be opened simultaneously with the closing of the pressure vessel 50, whereupon the container 14 can be emptied through the supply hose 54 by introducing pressure into the vessel 50.

When disc 30 is in the closed position shown in FIG. 8 and the nipple 32 may be pressed tightly against the solid part of the closure 29, liquid may be prevented from flowing out of the supply hose 54. Further, the described arrangement does not require a valve in the nipple 32, which would impede the volume flow and lead to higher cleaning expenditure.

Figure 11:
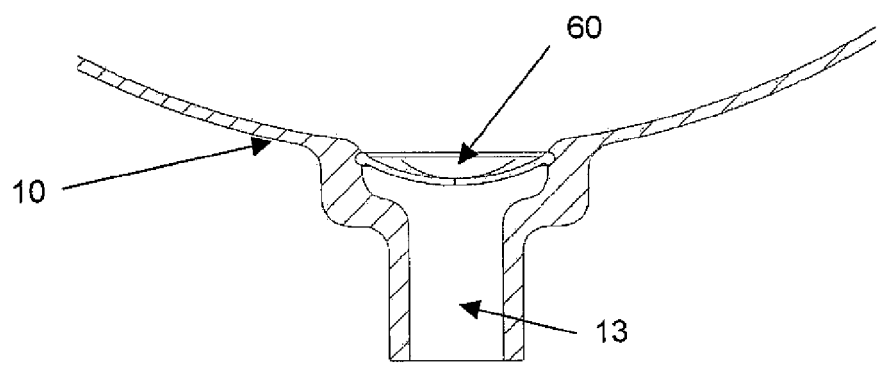
FIG. 11 is a section through a different embodiment of the lower part of the container having a closure diaphragm.
Figure 12:
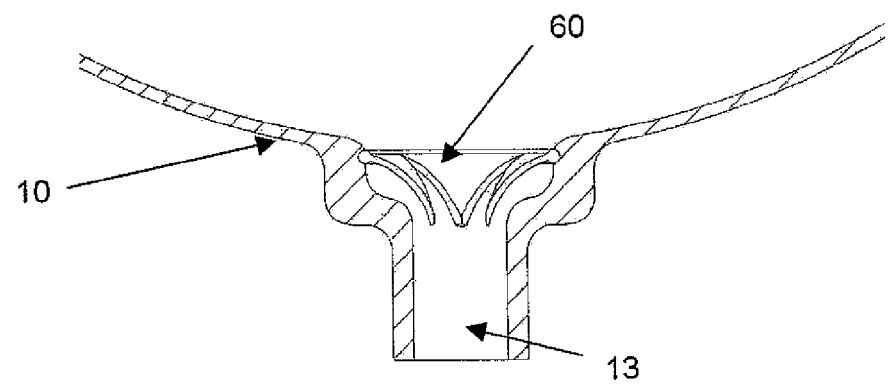
FIG. 12 is a representation corresponding to FIG. 11, showing the closure diaphragm opened.

In an alternative embodiment, a soft resilient slotted closure diaphragm 60 may be mounted directly at the outlet 13 of the container 14. The lower part is shown with the diaphragm 60 closed in FIG. 11 and open in FIG. 12. The diaphragm 60 provides sufficient resistance against an intentional flowing out of the liquid or sucking in of air during assembly.

Figure 13:
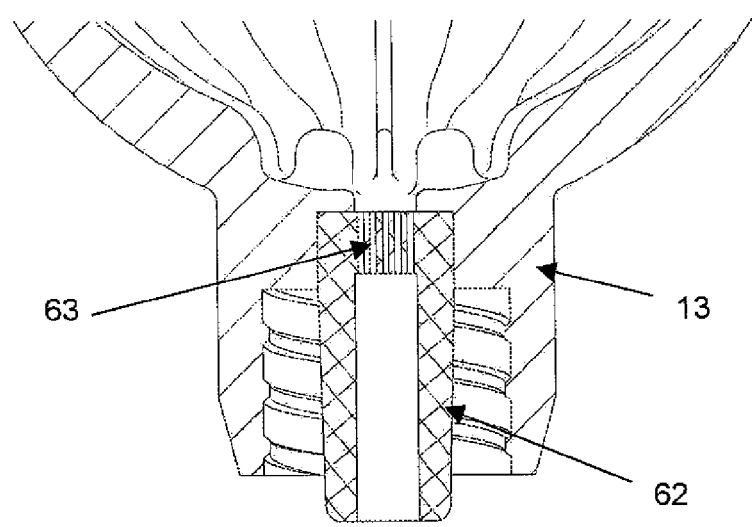
FIG. 13 is a section through a further embodiment of the lower part of the container having a different container outlet.

In a further alternative shown in FIG. 13, the diaphragm 60 may be replaced by an insert member 62 having fine through bores (capillaries) 63 (of a diameter of, e.g., 0.1 to 1.0 mm) which prevent an unintentional flowing out of the liquid due to their flow resistances.

The invention claimed is:

1. A container for uniformly metering flowable substances dispensed from the container, comprising:
 a rigid, concave, substantially hemispherical lower part having a region of largest diameter and being provided with an outlet and a plurality of inner grooves in contact with said flowable substances and extending radially to the outlet, the plurality of inner grooves being defined by a plurality of protruding webs;
 an upper part connected to the lower part in an air-tight manner in a region of the largest diameter and consisting of a flexible film having a convex shape mirror-inverted with respect to an inner wall of the lower part; and
 a body enclosing the upper part, connected to a flange of the lower part and open for entering of a pressure medium for emptying the container by pressure,
 wherein the protruding webs hold the flexible film at a distance from the outlet to enable the flowable substances to freely flow to the outlet until the container is completely empty,
 wherein the plurality of inner grooves have depths increasing toward the outlet as a result of a corresponding increase in heights of the plurality of protruding webs, in the direction toward the outlet to maintain uniform flow for the flowable substances being dispensed wherein the lower part has at least one inward protruding projection disposed near the outlet so as to prevent the film from impeding or inhibiting complete emptying by blocking the outlet.

2. The container of claim 1, wherein the body is closed by a double-walled cover including two disc-shaped walls of which have non-aligned pressure equalizing holes.

3. The container of claim 1, wherein the body is formed integrally with the flange.

4. The container of claim 3, wherein the body is cylindrical.

5. The container of claim 1, wherein the film forming the upper part is permeable to oxygen.

6. The container of claim 1, comprising a sensor provided at the lower part for detecting an abutment of the film at the inner wall of the lower part.

7. The container of claim 6, wherein the sensor is adapted for inductive or capacitive coupling with a metallic body provided on the film.

8. The container of claim 7, comprising a plurality of sensors positioned near the outlet.

9. The container of claim 1, wherein the flexible film is comprised of PE, PET or plastic composite film laminated with aluminium.

* * * * *